United States Patent
Zhang et al.

(10) Patent No.: US 9,303,006 B2
(45) Date of Patent: Apr. 5, 2016

(54) LINE LEAF INULA FLOWER LACTONE A AND METHODS FOR PREPARING AND USING THE SAME FOR TREATING MYOCARDITIS

(71) Applicant: SHANXI ZHENDONG PILOT BIOLOGICAL SCIENCE AND TECHNOLOGY CO., LTD., Jinzhong, Shanxi (CN)

(72) Inventors: Weidong Zhang, Shanghai (CN); Lei Shan, Shanghai (CN); Huizi Jin, Shanghai (CN); Juan Su, Shanghai (CN); Huiliang Li, Shanghai (CN); Yunheng Shen, Shanghai (CN); Xike Xu, Shanghai (CN); Runhui Liu, Shanghai (CN)

(73) Assignee: SHANXI ZHENDONG PILOT BIOLOGICAL SCIENCE AND TECHNOLOGY CO., LTD., Jinzhong (CN)

( * ) Notice: Subject to any disclaimer, the term of this patent is extended or adjusted under 35 U.S.C. 154(b) by 0 days.

(21) Appl. No.: 14/576,027

(22) Filed: Dec. 18, 2014

(65) Prior Publication Data
US 2015/0105457 A1    Apr. 16, 2015

Related U.S. Application Data

(63) Continuation of application No. PCT/CN2012/001306, filed on Sep. 25, 2012.

(30) Foreign Application Priority Data

Jun. 21, 2012  (CN) .......................... 2012 1 0208172

(51) Int. Cl.
- C07D 307/00   (2006.01)
- C07D 307/93   (2006.01)
- A61K 31/365   (2006.01)

(52) U.S. Cl.
CPC ............ *C07D 307/93* (2013.01); *A61K 31/365* (2013.01)

(58) Field of Classification Search
CPC .................................................... A61K 31/365
USPC ........................................................ 549/299
See application file for complete search history.

(56) References Cited

U.S. PATENT DOCUMENTS

2015/0105458 A1    4/2015  Zhang et al.

FOREIGN PATENT DOCUMENTS

| CN | 101830875 A | 9/2010 |
| KR | 20110087448 A | 8/2011 |

OTHER PUBLICATIONS

Nie et al. Journal of Natural Products (2010), 73(6), 1117-1120.*
Huang et al. Chinese Journal of Endermiology, 2000, 19(5), 330-332.*
Huang, Zhigang et al., "Relationship between nitric oxide and the development of viral myocarditis in mice," Chinese Journal of Endemiology, vol. 19, No. 5, pp. 330-332, ISSN 1000-4955 (Sep. 2000).
Nie, Li-Yue et al., "Sesquiterpenoids from *Inula lineariifolia* Inhibit Nitric Oxide Production," J. Nat. Prod., vol. 73, 1117-1120 (2010).

* cited by examiner

*Primary Examiner* — Nizal Chandrakumar
(74) *Attorney, Agent, or Firm* — Manni Li; Mei & Mark LLP

(57) ABSTRACT

Preparation and application of line leaf *inula* flower lactone A for treating myocarditis having a structure of

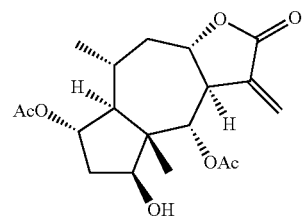

The compound shows positive therapeutic activity against Coxsackie virus and significant dose dependent correlation. The line leaf *inula* flower lactone A prevents disease in mouse models of experimental autoimmune myocarditis and onset of the process by intraperitoneal injection of a dose of 20 mg/kg/d. When increased to 100 mg/kg/d, the line leaf *inula* flower lactone A shows positive therapeutic effect on EAM. Line leaf *inula* flower lactone A is used as the sole active ingredient and combined with a conventional pharmaceutical carrier in a drug for treating myocarditis, and the pharmaceutical composition may be in the form of tablets, dispersible tablets, mouth collapse tablets, retard tablets, capsule, soft capsule, dropping pill, granules, injection, powder injection, or aerosol.

7 Claims, 2 Drawing Sheets

LINE LEAF INULA FLOWER LACTONE A AND METHODS FOR PREPARING AND USING THE SAME FOR TREATING MYOCARDITIS

CROSS-REFERENCE TO RELATED APPLICATIONS

The subject application is a continuation of PCT international application PCT/CN2012/001306 filed on Sep. 25, 2012, which in turn claims priority on Chinese patent applications CN 201210208172.9 filed on Jun. 21, 2012. The contents and subject matter of the PCT and Chinese priority applications are incorporated herein by reference.

TECHNICAL FIELD

The present invention relates to Chinese traditional medicine *inula* flowers, specifically, the preparation of *Inula Lineariifolia* lactone A from *inula* flowers and its application in the preparation of medicine for treating myocarditis.

BACKGROUND OF THE INVENTION

Myocarditis is localized or diffused myocardial inflammation that may originate in myocardium or occur as a part of a systemic disease. The pathological causes of myocarditis includes infection, physical-chemical factors, drug, etc., among which one of the most common is the viral myocarditis. In recent years, due to the widespread use of antibiotics for streptococcal infection, rheumatic fever caused by the infection has been gradually reduced, and rheumatic myocarditis has been significantly reduced. However, the pathogenesis of the viral myocarditis has been increasing. Viral myocarditis may be caused by a variety of virus infection, the most common being Coxsackie virus B. Sometimes, varicella and EB viruses may also cause viral myocarditis. Based on the research, about 5% of the viral infection would affect heart to cause the heart myocarditis. Virus infection will damage the cardiac muscle to cause the myocarditis. It may also be caused by autoimmune reaction after viral infection. The syndrome of viral myocarditis varies. Mild and localized lesions may have no symptoms, and the electrocardiogram (ECG) shows no abnormal performance, while the erythrocyte sedimentation rate (ESR) and myocardial enzyme index do not rise. Critical myocarditis patients have obvious symptoms, such as heart diffuse enlargement and heart failure, which causes significantly short of breath and inability to lie down. Some patients show arrhythmia, recurrent syncope, and sudden death. At present, the effect of the western medicine treatment of myocarditis is not ideal. For patients with viral myocarditis, there are no specific antiviral drugs, and the treatment effect on arrhythmia in patients with chronic myocarditis is poor. Traditional Chinese medicine has accumulated rich experience and shown obvious advantages in the prevention and treatment of myocarditis, lowers mortality, and reduces sequelae.

The line leaf *inula* flower (*Inula lineariifolia* Turcz. (syn. *Inula linariaefolia*)) is a perennial herb that belongs to the family of Asteracece and the genus of *Inula*, and has the common names of narrow-leaf *inula* flower, long-leaf *inula* flower, and small *inula* flower. They widely grow in the northeast, north, central, and eastern China, such as Henan, Hebei, and other provinces, and in Mongolia, North Korea, far east Russia, and Japan. It commonly grows in hills, wasteland, road, river, etc. Chinese traditional medicine *inula* flowers are the capitulum of the *inula* flowers or big flower *inula* flowers, and the entire herbal plant (gold boiling grass) may be used for medicinal purpose. Line leaf *inula* flowers have been used as the *inula* flowers in east China and other parts of China, and has been used for ventilation, diuresis, anti-inflammatory, softening hard masses, etc., and recorded in the Chinese Pharmacopoeia (1963 edition); however, line leaf *inula* flowers have ceased to be used as a medicine, as the patient, after being served, has the reactions of nausea, vomiting, etc.

SUMMARY OF THE INVENTION

The chemical composition of line leaf *inula* flowers have been investigated and a large number of sesquiterpenoids isolated by inventors for the subject application. See Li-Yue Nie et al., Journal of Natural Products, 2010, 73(6): 1117-1120. The present invention provides that further studies have found that line leaf *inula* flower lactone A shows therapeutic effects on myocarditis and is useful for developing novel medicine.

The present invention provides methods for extracting line leaf *inula* flower lactone A from line leaf *inula* flowers and applying it in preparing myocarditis treatment medicine.

The present invention provides a line leaf *inula* flower lactone A as a drug for treating myocarditis, and the line leaf *inula* flower lactone A has the following structure:

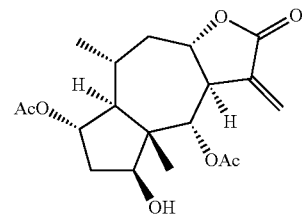 [SMILES: C=C1C(=O)O[C@H]2C[C@@H](C)[C@@H]3[C@@H](OC(C)=O)C[C@H](O)[C@@]3(C)[C@@H](OC(C)=O)[C@H]12]

Line leaf *inula* flower lactone A of the present invention is obtained as follows:

Dried line leaf *inula* flower grass is cut into pieces and extracted with 8~20 times (W/W) of 80~95% ethanol for 1 to 3 times, and each extraction lasts for 2 to 3 hours. The extracted solution from each extraction are combined and condensed into a liquid extract under the reduced pressure, and the liquid extract contains an equivalent of about 0.8 g to 1.2 g line leaf Inula flowers in 1 ml liquid extract. Water is added to dilute the liquid extract, and the amount of water added is 1 to 3 times the weight of the liquid extract. Then, the diluted liquid extract is extracted with 0.5 to 2 times (V/V) petroleum ether for 3 to 5 times, and the petroleum ether layer is obtained. The petroleum ether layer runs on a silica gel column chromatography, and is washed with 100:0 to 1:1 (V/V) petroleum ether/ethyl acetate gradient elution to separate the ingredients. After a thin-layer chromatography detection, an elution containing line leaf *inula* flower lactone A is collected, and run on a C18 reverse phase chromatography and washed with 50:100 to 70:100 (W/W) methanol/water gradient elution to purify. A thin-layer chromatography test confirms that a purified line leaf *inula* flower lactone A is obtained.

In the present invention, the experimental autoimmune myocarditis (EAM) model is used to test the medicinal efficacy of the compound in the following indicators for life protection in mice, life prolongation, weight, heart index, the effects of the pathological morphology and the cardiac function, serum neutralization antibody degree, and the degree of myocardial tissue virus drop test. The results show that the line leaf *inula* flower lactone A has activity against coxsackie virus, and the effect shows significant concentration-response correlation. Line leaf *inula* flower lactone A by intraperitoneal injection of 20 mg/kg/d prevents the occurrence of the EAM in mice; when the dose is increased to 100 mg/kg/d with intragastric administration, it also has certain curative effect. Therefore, line leaf *inula* flower lactone A may be used for preparing a drug for treating myocarditis.

In the present invention, line leaf *inula* flower lactone A is the sole active ingredient to be combined with conventional pharmaceutical carrier to prepare a drug for treating myocarditis. The drug may be in the form of tablets, dispersible tablets, mouth collapse tablets, retard tablets, capsule, soft capsule, dropping pill, granules, injection, powder injection, or aerosol.

DETAILED DESCRIPTION OF THE INVENTION

Figure 1:
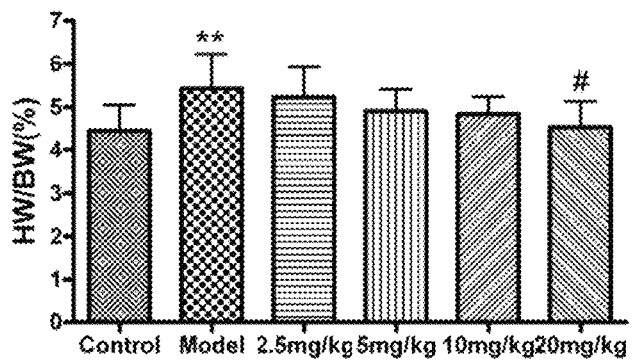
FIG. 1 shows the effect of the line leaf *inula* flower lactone A of the present invention on HW/BW of mice by intraperitoneal injection.

The following examples further describe the present invention in details but do not limit the scope of the present invention. One of ordinary skill in the art knows how to make modifications based on the examples without departing from the scope of the present invention.

Example 1

Preparation of Line Leaf Inula Flower Lactone A

Dried Line leaf *inula* flower grass 50 kg was cut into pieces, then extracted with 750 L ethanol (80~95% V/V) for two times, 2 hours each time. The extracts from each extraction were merged and under reduced pressure condensed into a liquid extract. The liquid extract contained the equivalent of 1 g Line leaf Inula flowers per milliliter. Water 750 L was added to diluted the liquid extract, then extracted 5 times with 50 L petroleum ether to get the petroleum ether layer. Volume at 100:0~1:1 petroleum ether/ethyl acetate gradient elution was used on silica gel column chromatography to separated the samples, thin-layer chromatography detection, collected the elution which contained line leaf *inula* flower lactone A. Weight for 50:100~70:100 methanol/water gradient elution was used to purify the extracts on C18 reverse phase chromatography, and a thin-layer chromatography test to get 45.3 g line leaf *inula* flower lactone A as the single product.

The obtained compound was tested by mass spectrometry to determine that the molecular weight was 366, and the molecular formula was $C_{19}H_{28}O_7$. Then, its carbon spectrum, hydrogen spectrum, and two-dimensional spectral data were obtained through the hydrogen nuclear magnetic resonance (NMR) analysis. The structural analysis was performed and it conformed with the data of the compound Line leaf Inula flowers lactone A.)

Example 2

Effect of Line Leaf Inula Flower Lactone A on Resistance of Coxsackie Virus in Mice A. Materials and Methods.

The thin Leaf *inula* flower lactone A compound from Example 1 was used; a viral strain: coxsackie B group virus B3 type Nancy strains (CVB3) was used at a virus infection dose of $10LD_{50}$ virus 0.2 ml through abdominal cavity infection in mice. The animals used were Balb/c male mice, 13 g to 15 g, from Shanghai West S&P-Bick Experimental Animals Co., Ltd. with animal number: qualified SCXX (Shanghai), 2008-0016. The positive control medicine was human recombinant interferon alpha 2 a, YinTeFen, Shenyang Junior Pharmaceutical co., Ltd., Product batch number 20090708.

Preparation and administration: the line leaf *inula* flower lactone A compound was weighed, ground, and suspended in 0.5% CMC (carboxymethyl cellulose) mixture at 10 mg/ml solution. Oral administration of the medicine was conducted for once per day, every time at 0.5 ml, for 7 days.

The experimental groups included (1) the viral infection group, each group had 10 mice, were given 0.5% CMC solution and virus. (2) The normal control group, each group had 10 mice, were given 0.5% CMC solution only. (3) Positive drug control group, each group had 10 mice, subcutaneous injections of recombinant interferon alpha 2 a suspended in 0.5% CMC solution, 15000 units per mouse, once every 2 days injection, a total of four injections. (4) High dose drug treatment group of 100 mg/kg, 10 mice in each group, oral give line leaf *inula* flower lactone A 50 mg/kg dose in drug treatment group, each group of 10, only oral give leaves Inula flowers lactone A. (5) Drug treatment of low dose group of 10 mg/kg, 10 in each group, oral give leaves Inula flowers lactone A. Observation parameters included life, neutralizing antibodies, virus protection, weight drops, myocardial tissue pathological slices, echocardiogram.

Test process was that after virus infection in mice (except the normal control group) for 2 hours, total drug delivery was performed 7 days in a row, observation was conducted until 14 days. The incidence and deaths were recorded every day, and the average survival days prolongation of life were calculated with p value calculation.

Another group of 10 mice, with infection, was weighed after 7 days. Four mice were taken to detect cardiac function, and killed and dissected for collecting blood to test neutralizing antibody, heart weighing calculation index, and grinding the heart, with three resistance MEM fluid containing 10%. 1:10 dilution, on the cell model to detect coxsackie virus in mice drop degree (to observe the myocardial cell lesions) separation of virus infection.

B. Results

TABLE 1

Life protection of line leaf inula flower lactone A on mice infected by CVB3

| Group | Number of animal | Survival time M (day) | SD | P |
|---|---|---|---|---|
| Virus control | 10 | 7.3 | 0.48 | |
| IFN | 10 | 8.4 | 2.11 | 0.12 |
| leaves Inula flowers lactone A 100 mg/kg | 10 | 9.4 | 2.5 | 0.018* |
| leaves Inula flowers lactone A 50 mg/kg | 10 | 9 | 1.89 | 0.013* |
| leaves Inula flowers lactone A 10 mg/kg | 10 | 8.9 | 1.85 | 0.017* |

Compared with virus group, *: P 0.05, or less * *: P 0.01 or less

Results showed that the treatment group of 100 mg/kg, 50 mg/kg, 10 mg/kg, had prolonged survival time, extended the percentage by 28.77%, 23.29%, 21.92%. Interferon prolonged the survival time, but there were no significant difference compared with the virus control group.

Results showed that 4 days after the virus infection, mice body weight significantly decreased, all mice were killed in the 8 days virus group, dose group mice body weight was increased, but there were still significant differences compared with normal group.

TABLE 2

Effect on the CVB3-Infected Mice Myocardial Virus in Mice to Measure at 7th Day.

| Group | NO | 1:10 | Lesions rate % | Average disease rate % | Reduce lesions |
|---|---|---|---|---|---|
| leaves Inula | 1 | ± | 25 | 40 | 55.56% |
| flowers | 2 | + | 50 | | |
| lactone A | 3 | + | 50 | | |
| 100 mg/kg | 4 | + | 50 | | |
| | 5 | ± | 25 | | |
| leaves Inula | 1 | ± | 25 | 55 | 38.89% |
| flowers | 2 | + | 50 | | |
| lactone A | 3 | + | 50 | | |
| 50 mg/kg | 4 | ++ | 100 | | |
| | 5 | + | 50 | | |
| leaves Inula | 1 | + | 50 | 60 | 33.33% |
| flowers | 2 | + | 50 | | |
| lactone A | 3 | + | 50 | | |
| 10 mg/kg | 4 | + | 50 | | |
| | 5 | ++ | 100 | | |
| IFN | 1 | ± | 25 | 45 | 50.00% |
| | 2 | + | 50 | | |
| | 3 | + | 50 | | |
| | 4 | + | 50 | | |
| | 5 | + | 50 | | |
| Virus control | 1 | ++ | 100 | 90 | 0 |
| | 2 | ++ | 100 | | |
| | 3 | ++ | 100 | | |
| | 4 | + | 50 | | |
| | 5 | ++ | 100 | | |
| Normal | 1 | − | 0 | 0 | |
| controls | 2 | − | 0 | | |
| | 3 | − | 0 | | |
| | 4 | − | 0 | | |

−: 0%,
plus or minus: 0%,
: + 50%,
++ 100%

Results showed that myocardial after virus infection could infect host cells to cause pathological changes, the virus group had the myocardial cellular pathological changes induced by the virus in the lesions as high as 90%. Line leaf *inula* flower lactone A had inhibitory effect on the coxsackie virus replication in the myocardial, and at 100 mg/kg in the treatment group, the cell pathological changes were reduced to 40%.

TABLE 4

Effect on Serum Neutralizing Antibody in the CVB3-Infected Mice

| Group (n = 4) | 1: X (7 days) | 1: X (14 days) |
|---|---|---|
| 100 mg/kg | 1: 169 | 1: 250 |
| 50 mg/kg | 1: 139 | 1: 250 |
| 10 mg/kg | 1: 74 | 1: 250 |
| IFN | 1: 1250 | 1: 1250 |

TABLE 3

Effect on Live Body weight in CVB3-Infected Mice

| Group | Before M ± SD | Before P | 4 days M ± SD | 4 days P | 8 days M ± SD | 8 days P | 14 days M ± SD | 14 days P |
|---|---|---|---|---|---|---|---|---|
| Virus | 14.65 ± 0.59 | 1 | 12.84 ± 0.92 | 0** | | | | |
| 100 mg/Kg | 14.57 ± 0.55 | 0.75 | 15.13 ± 0.88 | 0.00021** | 16.1 ± 1.05 | 0** | 18.21 ± 0.86 | 0** |
| 50 mg/Kg | 14.58 ± 0.49 | 0.77 | 15.14 ± 0.68 | 0** | 16.03 ± 0.96 | 0** | 18.33 ± 0.80 | 0** |
| 10 mg/Kg | 14.59 ± 0.71 | 0.84 | 15.23 ± 1.01 | 0** | 15.59 ± 0.89 | 0** | 17.92 ± 1.10 | 0** |
| IFN | 14.53 ± 0.59 | 0.65 | 14.80 ± 1.50 | 0.0016** | 15.82 ± 0.47 | 0** | 18.07 ± 0.88 | 0** |
| Normal | 14.65 ± 0.56 | | 16.77 ± 0.75 | | 19.06 ± 0.77 | | 22.65 ± 1.03 | |

All group compared with normal group,
**P 0.01, or less
*P 0.05 or less

TABLE 4-continued

Effect on Serum Neutralizing Antibody in the CVB3-Infected Mice

| Group (n = 4) | 1: X (7 days) | 1: X (14 days) |
|---|---|---|
| Virus controls | 1: 96 | |
| Normal controls | 1: 50 | 1: 50 |

In Table 4, 1: X referred to serum dilution ratio, and the higher the diluted times, the stronger the ability for neutralizing antibodies. Results showed that line leaf *inula* flower lactone A improved the neutralizing antibodies in the CVB3-infected mice, and by 7 days, certain concentration-response relationship was established.

Example 3

Line Leaf Inula Flower Lactone A Treatment in the Mouse EAM Model 3.1. EAM Model Pig myocardial myosin (PCM, 1 mg/ml; Sigma, St. Louis, Mo.) (Sigma), and equal volume of Freund's Complete Adjuvant (FCA, Sigma St. Louis, Mo.), were in an uniform emulsification and mixed into a homogeneous emulsion, where the *mycobacterium tuberculosis* H37Ra bead (Difco, Detroit, Mich.) with final concentration at 5 mg/ml. In the 0th day, the emulsion 0.2 ml (including antigen 200 µg) was taken and subcutaneously administered at the bilateral inguinal and multiple points under the armpit in mice. Seven days after the first immunization, the same procedure was performed to strengthen the immune once. The animals were divided into groups, each group had six mice.

3.2. Administration Route

Beginning on the day of immunity, the mice were given line leaf *inula* flower lactone A continuously for 21 days. Two dosing methods were applied:

(1) intraperitoneal injection: Line leaf *inula* flower lactone A of Example 1 was dissolved in phosphate buffer solution (PBS) (containing 5% DMSO (dimethyl sulfoxide)). The 4 concentration gradients were at 2.5 mg/kg/d$^{-1}$ (2.5 mg/kg every time, once a day); 5 mg/kg/d$^{-1}$; 10 mg/kg/d$^{-1}$; and 20 mg/kg/d$^{-1}$.

(2) Intragastric Administration: Line leaf *inula* flower lactone A suspended in 0.5% CMC-Na (carboxymethyl cellulose sodium). The 3 concentration gradients were at: 10 mg/kg/d$^{-1}$; 50 mg/kg/d$^{-1}$; and 100 mg/kg/d$^{-1}$.

3.3. Results of the Experiment.

Mice after 21 days were killed by taking off the neck, shearing heart, weighing and take photos, pathological section (HE hematoxylin-eosin staining), cytokine TNF-α change.

(1) heart and body weight ratio (HW/BW). Myocarditis in mice after the onset of the myocarditis should have the heart weight/body weight ratio larger than the model group, if the medication was effective, the ratio should be small and close to the normal group. Experimental results found that intraperitoneal injection of line leaf *inula* flower lactone A at 20 mg/kg/d$^{-1}$ had changed HW/BW significantly as shown in FIG. 1.

Figure 2:
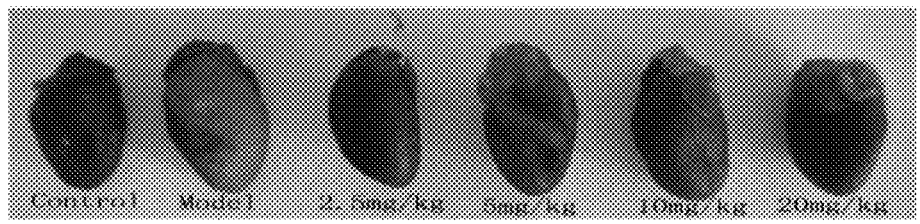
FIG. 2 shows the effect of the line leaf *inula* flower lactone A of the present invention on the cardiac morphology of mice after intraperitoneal injection.
Figure 3:
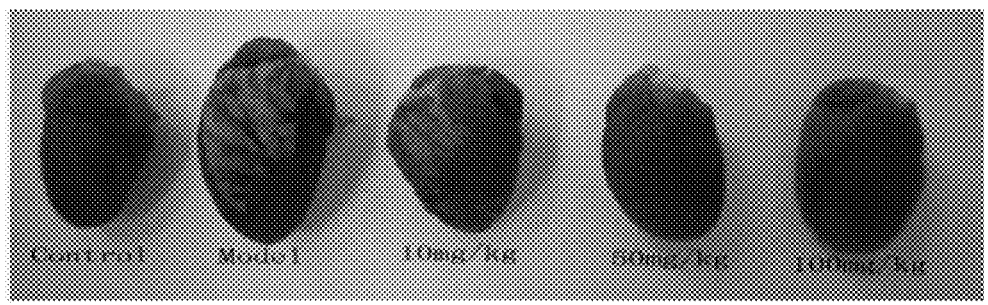
FIG. 3 shows the effect of the line leaf *inula* flower lactone A of the present invention on cardiac morphology of mice after intragastric administration.

(2) Cardiac morphology. After the onset of the EAM in mice, the heart appeared swelling and pale as the result of the infiltration by inflammatory cells. Intraperitoneal injection of the line leaf *inula* flower lactone A (XX-3) were given at various dosages. While cardiac pathology such as various degrees of swelling and lesion was observed in animals of all dosage groups, compared with the model group and solvent control group, the treatment groups showed that the degree and extent of the lesion had various degrees of improvement, leading to the conclusion that the reagent had certain effect on the target myocardial inflammation in mice, of which, 20 mg/kg/d$^{-1}$ worked the best efficacy. The experimental results of intragastric administration also showed that line leaf *inula* flower lactone A has curative effect on the EAM model with the most effective dose at 20 mg/kg/d$^{-1}$ as shown in FIGS. 2 and 3.

(3) TNF-α change. TNF-α was an inflammation factor that played an important role in the onset of the EAM. Twenty-one (21) days after the first immunization, blood was collected from the orbital venous plexus and placed in an anticoagulant tube and centrifuged at 3000 r/min to obtain serum specimen and frozen and stored at −20° C.

Figure 4:
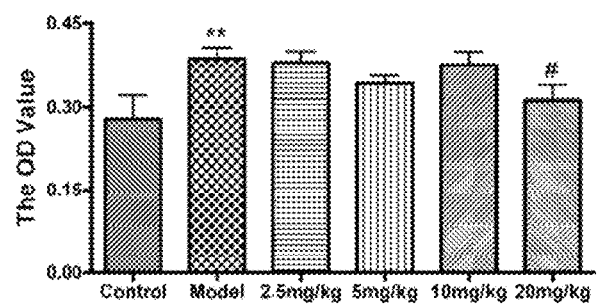
FIG. 4 shows the effect of the line leaf *inula* flower lactone A of the present invention on TNF-a by intraperitoneal injection.

Test results were shown in FIG. 4, in the model group at 21 days after the primary immune, the expression of serum TNF-α significantly increased (**$P<0.01$) compared with the control group. Comparing the group with intraperitoneal injection of line leaf *inula* flower lactone A with the model group, the levels of serum TNF-α both decreased while in the 20 mg/kg group the difference was significant (#$P<0.05$).

Comparing the model group with the blank group, * * $P<0.01$; 20 mg/kg group compared with the model group, # $P<0.05$.

Figure 5:
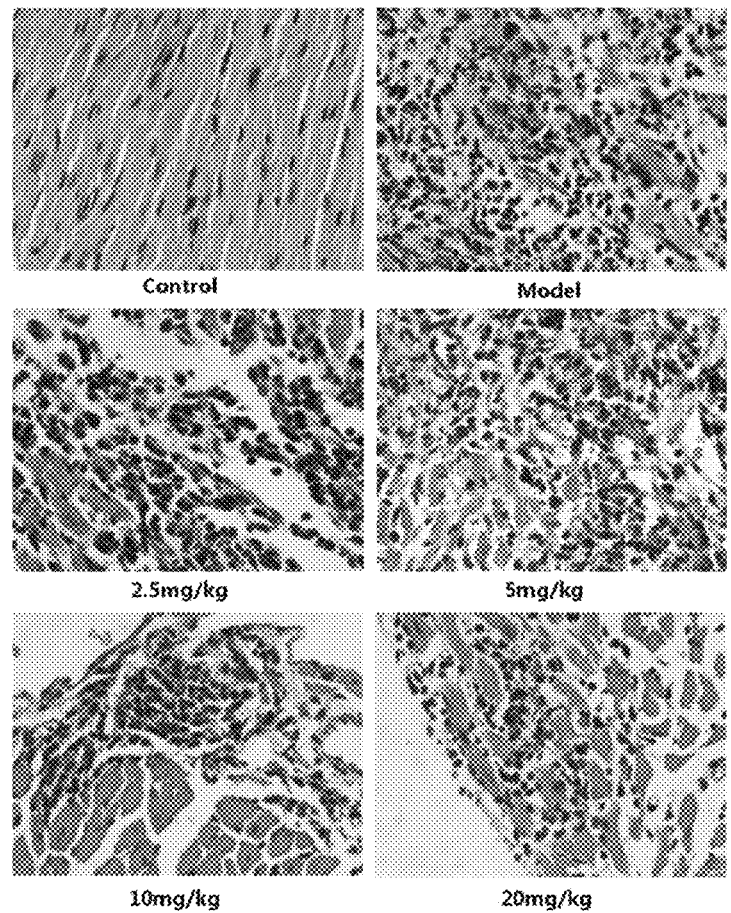
FIG. 5 shows the HE staining of mice cardiac muscle after treated by the line leaf *inula* flower lactone A of the present invention (intraperitoneal injection).

(4) pathology (conventional HE staining). Mice were killed by taking off the neck, heart was taken out, and residual blood was removed. Each heart was fixed in 10% formaldehyde, paraffin embedded, continuous sliced with conventional HE staining and observed under the microscope. The model group had visible focal myocardial cell degeneration necrosis, cytoplasm red dye, nuclear disappeared, with some muscle dissolved, interstitial broadening, and various inflammatory cell infiltration. The control group did not show obvious anomalies, as shown in FIG. 5.

In the groups of animals administered with various dosages, the heart tissue slices showed myocardial cell focal necrosis and calcification or had different degree of flake myocardial inflammatory lesions, such as oven. However, when comparing the lesions of the treated groups with the model group and solvent control group, the degree and extent of lesion were different with different degrees of improvement, indicating that the line leaf *inula* flower lactone A had curative effect on myocardial inflammation in mice, and intraperitoneal injection at 20 mg/kg·d$^{-1}$ and intragastric administration at 100 mg/kg·d$^{-1}$ worked the best (both were the highest dose in our experiments).

Example 4

Tablet Preparation

Line leaf *inula* flower lactone A 50 g, lactose 280 g, and corn starch 62 g were mixed and uniformed wet by water. The wet mixture was sieved (16 mesh) and dried (at 60° C. for 30 min), re-screened (14 mesh). Magnesium stearate 8 g was added and the mixture was pressed to form tablet, each piece weighed 400 mg and contained 50 mg line leaf *inula* flower lactone A.

Example 5

Composition for Injection

Line leaf *inula* flower lactone A 6 g and 50 g glucose were dissolved in suitable amount of water for injection and filtered to obtain a solution. Under aseptic conditions, the solution was added to the infusion bottle (100 ml per bottle), and each bottle contained 6 mg line leaf *inula* flower lactone A.

Example 6

Freeze-Dried Powder for Injection

Line leaf *inula* flower lactone A 60 g and mannitol 240 g were dissolved in the suitable amount of water for injection use, filtered, stored under aseptic conditions in Schering bottles (10 ml Schering bottles, 2 ml per bottle), and freeze-dried. Each bottle contained line leaf *inula* flower lactone A 60 mg.

We claim:

1. A method for treating myocarditis comprising administering to a subject in need of treatment for myocarditis a therapeutically effective amount of the pharmaceutical composition comprising
a compound being a line leaf *inula* flower lactone A having a structure of

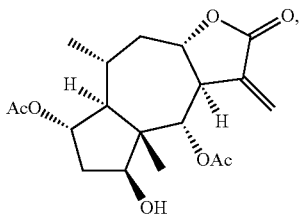 [SMILES: C=C1C(=O)O[C@H]2C[C@@H](C)[C@@H]3[C@@H](OC(C)=O)C[C@H](O)[C@@]3(C)[C@@H](OC(C)=O)[C@H]12]

wherein the amount of the line leaf *inula* flower lactone A in the pharmaceutical composition is about 10 mg to 100 mg per kilogram of weight of a subject to be treated for myocarditis.

2. The method for treating myocarditis according to claim 1, wherein the line leaf *inula* flower lactone A is sole active ingredient in the pharmaceutical composition.

3. The method for treating myocarditis according to claim 1, wherein the pharmaceutical composition is in a form of tablets, dispersible tablets, mouth collapse tablets, retard tablets, capsule, soft capsule, dropping pill, granules, injection, powder injection, or aerosol.

4. The method for treating myocarditis according to claim 1, wherein the pharmaceutical composition comprises a pharmaceutically acceptable carrier.

5. The method for treating myocarditis according to claim 4, wherein the line leaf *inula* flower lactone A is sole active ingredient that is combined with the pharmaceutically acceptable carrier in the pharmaceutical composition.

6. The method for treating myocarditis according to claim 4, wherein the pharmaceutical composition is in a form of tablets, dispersible tablets, mouth collapse tablets, retard tablets, capsule, soft capsule, dropping pill, granules, injection, powder injection, or aerosol.

7. The method for treating myocarditis according to claim 1, wherein the pharmaceutical composition is administered by intraperitoneal injection or intragastric administration.

* * * * *